United States Patent [19]

Aswal et al.

[11] Patent Number: 5,145,955
[45] Date of Patent: Sep. 8, 1992

[54] PROCESS FOR THE PREPARATION AND COMPOSITION OF A FRACTION CONTAINING PICROSIDE I AND KUTKOSIDE

[75] Inventors: Bacchan S. Aswal; Ramesh Chander; Sunil K. Chatterji; Bhola N. Dhawan; Yogesh Dwivedi; Narendra K. Garg; Poonam Jain; Narinder K. Kapoor; Dinesh K. Kulshreshtha; Bishan N. Mehrotra; Gyanendra K. Patnaik; Ravi Rastogi; Jagat P. S. Sarin; Krishna C. Saxena; Shekhar C. Sharma; Shri K. Sharma; Binduja Shukla; Pradeep K. S. Visen, all of Lucknow, India

[73] Assignee: Council of Scientific & Industrial Research, New Delhi, India

[21] Appl. No.: 783,410

[22] Filed: Oct. 28, 1991

[51] Int. Cl.$^5$ .................. A01N 65/00; A65K 35/78

[52] U.S. Cl. .................. 536/124; 424/195.1; 514/893; 514/894

[58] Field of Search .................. 424/195.1; 536/124; 514/893, 894

[56] References Cited

U.S. PATENT DOCUMENTS

| | | | |
|---|---|---|---|
| 4,401,825 | 8/1983 | Weinges et al. | 560/121 |
| 4,764,372 | 8/1988 | Herrnstadt et al. | 514/2 |
| 4,867,978 | 9/1989 | Gold | 424/709 |
| 4,880,624 | 11/1989 | Metcalf | 424/84 |
| 5,026,550 | 6/1991 | Aeschbach et al. | 424/195.1 |
| 5,049,380 | 9/1991 | Grossman et al. | 424/195.1 |
| 5,093,122 | 3/1992 | Kodera | 424/195.1 |
| 5,096,708 | 3/1992 | Gohla et al. | 424/195.1 |

Primary Examiner—Ronald W. Griffin
Attorney, Agent, or Firm—Ladas & Parry

[57] ABSTRACT

The present invention describes a process for the preparation of a fraction, mainly containing picroside I and kurrooa, from the plant *Picrorhiza kurrooa*.

10 Claims, No Drawings

PROCESS FOR THE PREPARATION AND COMPOSITION OF A FRACTION CONTAINING PICROSIDE I AND KUTKOSIDE

This invention relates to a process for the preparation and composition of a fraction, mainly containing picroside I and kutkoside (designated by us as picroliv), from the plant *Picrorhiza kurrooa* as well as the biological activities of picroliv viz. hepatoprotective, choleretic, anticholestatic, anti-hepatitis B virus like and immunostimulant.

*Picrorhiza kurrooa* is an erect perenial herb about 15 to 25 cm high, growing in Alpine Himalayas from Kashmir to Sikkim, 9,000–15,000 ft. The common trade and vernacular name of the herb is kutki (R. N. Chopra et al., Indigenous Drugs of India, 182, 1958). The root has a bitter sharp taste and is a valued drug for liver complaints and biliousness. (K. R. Kirtikar et al., Indian Medicinal Plants III, 1825-26, 1933).

The ever increasing environmental pollution, exposure to industrial toxicants, food adulteration, malnutrition, unjudicious use of drugs, excessive consumption of alcohol and certain infections lead to various kinds of liver disorders. This poses one of the major challenges in the health care programmes of any country developed or under developed. Present however, no effective therapy is available for the treatment of various liver ailments.

DETAILED DESCRIPTION OF THE INVENTION

Picroliv is a standardised fraction of the ethanolic extract of *Picrorhiza kurrooa*. It consists of (a) 1a,1b,2-,5a,6,6a-hexahydro-6-hydroxy 1a (hydroxymethyl)-oxireno[4,5]cyclopenta(1,2-c)pyran-2-yl-6-(3-phenyl-2-propanoate), [1aS-(1a$\alpha$,1b$\beta$,2$\beta$(E),5a$\beta$,6$\beta$,6a$\alpha$)]-$\beta$-D-glucopyranoside (picroside I) (b) 1a,1b,2,5a,6,6a-hexahydro-6-hydroxy-1a[(4-hydroxy-3-methoxybenzoyl)oxy]methyl]oxireno[4,5]cyclopenta[1,2-c]pyran-2-yl-$\beta$-D-glucopyranoside(kutkoside) (c) a fraction (named as F006) containing 4–5 cucurbitacin glycosides and (d) an intractable mixture of other minor unidentified substances, the amount of (a) and (b) ranging from 50–70%, the ratio of (a) and (b) being 1:1.5 to 1:2, the amount of (c) being 4–5% and that of (d) 26–45%. Elution profiles of picroliv and cucurbitacin glycoside fraction (F006) on HPLC on C-18 reverse phase column using a solvent system acetonitrile:water:acetic acid (25:75:0.5) are given in FIGS. 1 and 2 respectively.

Process for the preparation of picroside I and kutkoside individually in a mixture from the plant *Picrorhiza kurrooa* is known. The fraction containing cucurbitacin glycosides from picroliv was prepared and designated by us as F006. Picroliv was saponified by stirring with a saturated solution of barium hydroxide for six hours followed by extraction with ethyl acetate. The organic layer was washed once with sodium bicarbonate solution followed by two washings with water, dried over anhydrous sodium sulphate and evaporated. The residue contained mixture of cucurbitacin glycosides (F006). One of the cucurbitacin glycosides present in picroliv was isolated by column chromatography over silica gel using ethyl acetate and mixtures of ethyl acetate containing various proportions of methanol as eluant. Ethyl acetate:methanol (9:1) eluate gave an impure cucurbitacin glycoside which was further purified by preparative thin layer chromatography over silica gel plates using ethyl acetate:methanol (9:1) as the solvent system. The pure compound was identical with 25-acetoxy-2$\beta$-D-glucopyranoxy-3,16,20-trihydroxy-9-methyl-19-norlanosta-5,23-diene-22-one (III) reported by Laurie et al. (Phytochemistry 24 (1985), 2659).

Rastogi et al. (J. Sci. Ind. Res., 8B (1949) 173, 18B (1959) 219) reported the isolation of a bitter glycoside, named as kutkin, along with vanillic acid and mannitol, while Rastogi et al. (J. Sci. Ind. Res., 14B (1955) 512) characterised kutkin as 6-cinnamoyl-$\beta$-D-glucosidovanillate, Basu et al. (J. Org. Chem., 35 (1970) 3159) assigned it 4'-cinnamoyl vanilloyl glucoside structure. Rastogi et al. also attempted the synthesis of kutkin (J. Sci. Ind. Res., 18B (1959) 522). Kitagawa et al. (Tetrahedron Lett. (1969) 3837; Chem. Pharm. Bull. 19 (1971) 2534) isolated picroside I and characterised it as 6'-O-cinnamoyl catalpol. Later B. Singh et al. (Indian J. Chem. 10 (1970) 29) found that kutkin was a mixture of picroside I and another glycoside designated as kutkoside. Kutkoside was characterised as 10-O-vanilloyl catalpol. Klaus et al. isolated two more glycosides viz. picroside II (6-O-vanilloyl catalpol) and picroside III (6'(4-hydroxy-3-methoxy cinnamoyl)catalpol) from the plant in addition to a mixture of 6-cinnamoyl-$\alpha$- and 6-cinnamoyl $\beta$-D-glucopyranose which are presumably formed by the cleavage of picroside I during work up (Ann. Chem. 759 (1972) 173; Ann. Chem. (1977) 1053). Isolation and characterisation of fifteen more cucurbitacin glycosides and an aglycon are also reported from this plant (Hermann Stuppner et al., Planta Med. 55 (1989), 559; Hermann Stuppner et. al., Phytochemistry, 29, (1990), 1633; Hermann Stuppner et. al., Phytochemistry, 30, (1991), 305).

German patent No. 2.203,884 reports a process for the isolation of picroside II (1a,1b,2,5a,6,6a hexahydroxy-6-[(4-hydroxy-3-methoxybenzoyl)oxy]-1a-(hydroxymethyl)oxireno[4,5]-cyclopenta[1,2-c]pyran-2-yl[1aS(1a$\alpha$,1b$\beta$,2$\beta$,5a$\beta$,6$\beta$,6a$\alpha$)]-$\beta$-D-glucopyranoside).

It has been observed by us in the paper entitled 'Hepatoprotective activity of kutkin, the iridoid glycoside mixture of *Picrorhiza kurrooa*, published in Indian J. Med. Res., 87 (1988) 401, that the alcoholic extract of the root and/or rhizome of *Picrorhiza kurrooa* showed significant hepatoprotective activity before the chromatographic separation of the individual compound picroside I and kutkoside. It was also disclosed in the said paper that the mixture of picroside I and kulkoside i.e. kutkin exhibited higher hepatoprotective activity as compared to the individual compounds. So far no process has been described to isolate a fraction from the plant *Picrorhiza kurrooa* having hepatoprotective choleretic, anticholestatic, antihepatitis B vial and immunostimulant properties. The objective of the present invention is to provide a process for the preparation and composition of a fraction from the plant *Picrorhiza kurrooa* having hepatoprotective choleretic, anticholestatic, anti-HBs Ag like and immunostimulant properties without employing chromatographic methods. The fraction obtained by the process of the present invention has the property to prevent hepatotoxicity and also exhibit significant immunostimulant properties in humans and experimental animals and therefore is useful in the prevention/treatment of liver damage produced by various hepatotoxic agents and in the treatment of infective hepatitis and other related hepatic infections.

The main finding underlying the invention is that by a process of fractionation with different polar solvents of the alcoholic extract of the root and/or rhizome of *Picrorhiza kurrooa* a fraction is obtained, which mainly consists of a mixture of pharmacologically active picroside I and kutkoside in an amount of 50 to 70%, the ratio being 1:1.5 to 1:2 and a mixture of cucurbitacin glycosides to the extent of 4 to 5% along with other unidentified substances in an amount 26 to 45%.

Picroliv is light yellowish brown amorphous powder, bitter in taste. It is insoluble in hexane, benzene and chloroform, soluble in acetone, ethanol, methanol and water. Picroliv has shown a potent hepatoprotective, choleretic, anticholestatic antihepatitis B viral as well as immunostimulant activities. The hepatoprotective activity of picroliv has been evaluated against hepatic damage induced by various agents viz. galactosamine, paracetamol thioacetamide, carbon tetrachloride, lanthanum chloride, monocrotaline, ethylalcohol, aflatoxin, *Amamita phalloides* toxin, cycloheximide in rat and *Plasmodium berghei* infection in mastomys. The assessment of activity was based on the changes brought about by the hepatotoxic agents in various serum and tissue biochemical parameters (Table 1) and also by histopathological examination of liver. Picroliv brought about 48 to 100% reversal of changed parameters at doses varying from 3 to 12 mg/kg p.o.×7 days (Table 2). The severity of the histopathological changes also became normal in picroliv treated animals.

In the isolated hepatocyte preparation the, hepatoprotective activity was assessed against paracetamol, galactosamine carbon tetrachloride and thioacetamide induced damage. At the dose levels of 1.5 to 12 mg/kg p.o.×7 days, picroliv showed a wide range of protection (Table 3) as evident by reversal of altered biochemical parameters (GOT, GPT and ALP) and increased percentage of viable cells which was determined by Trypan blue exclusion test and oxygen uptake by the cells.

Picroliv showed dose dependent (1.5–12 mg/kg p.o.×7 days choleretic effect in conscious rats and anaesthetized guinea pigs and cats. It produced significant anticholestatic effect against paracetamol, carbon tetrachloride and ethinyl estradiol induced cholestasis and also antagonised to a large extent the reduction in the volume of bile along with the bile contents (bile salts end bile acids) at the dose level of 6 to 12 mg/kg.

TABLE 1

Biochemical parameters used in the evaluation of hepatoprotective activity

| IN LIVER AND SERUM | IN SERUM ONLY | IN LIVER ONLY |
|---|---|---|
| a) Total proteins | Albumen | DNA |
| b) Cholesterol | Triglycerides | RNA |
| c) Phospholipids | Lipoprotein-X | Glycogen |
| d) Acid phosphatase | VLDL + LDL | Total lipids |
| e) Alkaline phosphatase | HDL | Lipid peroxides |
| f) Glutamic oxaloacetate transaminase | Glutamate dehydrogenase | Succinate dehydrogenase |
| g) Glutamic pyruvate transaminase | Bilirubin | Glucose-6-phosphatase |
| h) Lactate dehydrogenase | | Acid ribonuclease |
| i) | | 5'-Nucleotidase |
| j) | | γ-Glutamyl transpeptidase |
| k) | | Superoxide dismutase |
| l) | | Cytochrome P-450 |

TABLE 1-continued

Biochemical parameters used in the evaluation of hepatoprotective activity

| IN LIVER AND SERUM | IN SERUM ONLY | IN LIVER ONLY |
|---|---|---|
| m) | | Cytochrome $b^5$ |

TABLE 2

Reversal of hepatotoxin induced altered biochemical parameters by picroliv

| Sl. No. | Hepatotoxin | Picroliv (mg/kg po) | Percent reversal |
|---|---|---|---|
| 1. | Galactosamine | 3–12 × 7 | 25–100 |
| 2. | Paracetamol | 3–12 × 7 | 30–100 |
| 3. | Thioacetamide | 3–12 × 7 | 20–100 |
| 4. | Monocrotaline | 25 × 12 | 70–100 |
| 5. | Aflatoxin $B_1$ | 25 × 7 | 25–100 |
| 6. | Lanthanum | 25 × 7 | 30–100 |
| 7. | $CCl_4$ | 3–12 × 15 | 15–100 |
| 8. | *Amanita phalloides* | 25 × 10 | 40–100 |
| 9. | Ethanol | 3–12 × 7 | 40–90 |
| 10. | Cycloheximide | 12 × 7 | 80–100 |
| 11. | *Plasmodium berghei* infection in mastomys | 3–12 × 15 | 10–98 |

TABLE 3

Effect of picroliv on isolated rat hepatocytes (Ex-vivo)

| Hepatotoxin | Picroliv (mg/kg p.o. × 7) | % Reversal Viability | % Reversal Biochemical |
|---|---|---|---|
| Galactosamine | 3–12 | 40–100 | 28–100 |
| Paracetamol | 1.5–12 | 35–100 | 30–100 |
| Thioacetamide | 1.5–12 | 18–100 | 20–100 |
| Carbon tetrachloride | 1.5–12 | 15–100 | 18–100 |

The effect of long term administration of picroliv to weaning rats was also observed. Doses of 6–12 and 25 mg/kg p.o. were given for 2 months. At the end of the experiment improved growth rate as well as rate of bile flow (12–61%) was observed in the picroliv treated rats as compared to controls. In the picroliv treated animals no change was observed in the fasting blood glucose level and the values of different liver and serum parameters except cytochrom P 450. However, an increased uptake of $^{14}C$ glucose, $^{14}C$ leucine and $^{14}C$ acetate by 80, 30 and 25% respectively was observed in picroliv fed rats (25 mg/kg p.o.) as compared to normal hepatocytes.

Picroliv was tested for the presence of antihepatitis B virus surface antigen (anti HBs) like activity. HBs Ag positive serum samples obtained from hepatitis B virus (HBV) associated acute and chronic liver diseases and healthy HBs Ag carriers were used to evaluate the anti-HBs like activity of picroliv. It was mixed with serum samples and incubated at 37° overnight followed by HBs Ag screening in ELISA system.

Picroliv brought about reduction in HBs Ag titre in 100% serum samples. In case of HBs Ag carriers and cirrhosis patients picroliv (4 mg/ml) showed 4.5 and 4 fold reduction in HBs Ag titre respectively while in the samples from the patient of acute viral hepatitis (AVH) 3.8 fold reduction was observed. Picroliv also affected the HBs Ag titre in 75% serum samples with a mean reduction of 2±0.4 fold.

Picroliv showed reduction in HBs Ag titre after dilution of the antigen in the serum samples. The reduction increased with increasing dilution of antigen samples and reached a maximum at 1:1024 dilution. Picroliv also caused inhibition of purified HBs Ag and HBe Ag. Although in low concentrations (0.1 to 2.0 mg/ml) it had no effect on HBs Ag. But at 2.5 to 4 mg/ml concentration (0.039 μg/ml) HBs Ag was inhibited. Further increase in concentration (5-10 mg/ml) increased HBs Ag inhibition (0.156 mg/ml) but a stepwise dose related response was not observed. In a concentration of 2-6 mg/ml it produced an inhibition of 0.004 μg/ml HBe Ag. With further increase (up to 10 mg/ml) there was only a slight improvement. Thus inhibition of HBs Ag was maximum at 5 mg/ml, while that of HBe Ag was maximum a 2 mg/ml. With both the antigens, increase in picroliv concentration beyond a certain level did not lead to further enhancement in activity.

Picroliv produced an inhibition in HBV-DNA. The extent of inhibition was dependent on the HBV-DNA content in serum samples. Serum samples with low DNA content showed only 4% inhibition on picroliv treatment. In the serum samples with high HBV-DNA (392 μg/ml), 15.7% inhibition was produced by picroliv. Picroliv affected HBV-DNA in 65% serum samples.

The in vivo effect of picroliv on HBV has been evaluated in Pekin duck. The carrier state of the DHBV and its sequlae are similar to HBV infection. The transmission of DHBV occurs vertically similar to HBV infection in man. If the DHBV infection occurs during early period of life just after hatching, the animals become persistently viremic. It is, therefore, possible using this experimental model of HBV to evaluate any compound for interruption of an established carrier state as well as for its ability to prevent development of carrier state. The sets of experiments were planned to screen the effects of picroliv against human hepatitis B virus using Pekin duck as an animal model for both these investigations.

The dose of picroliv was 25 mg/bird, ip daily for a period of 28 days. Based on the initial observations with some of the above products, it was decided to increase the dose to 50 mg per duck daily for a longer period. The dose was given i.p. under aseptic condition. In each set of experiment there were 8 ducks.

In animals which were treated for 28 days (25 mg of picroliv) were followed up for 10 weeks after stopping treatment. With higher dose (50 mg/animal/day), a much longer period of follow-up has been planned. The animals were sacrificed after the stoppage of administration of picroliv at different intervals (4,8,12,16,20 wks). The serum was separated and used for virological studies. During autopsy, major parenchymatous organs (liver, pancreas, kidney, heart and lungs) were collected. The tissues were fixed in buffered formalin and after routine fixation and paraffin embedding the sections were cut and stained with H and E. Since it has been established by in vitro experiments that picroliv binds with the hepatitis B surface antigen present in the serum sample thereby demonstrating anti-HBs like activity. This activity differs from a classical virus neutralization. In order to confirm the in vitro experiments in vivo experiments were carried out.

The DHBV (+) serum sample (200 μl) obtained from persistently viremic duck was mixed with 200 μl of picroliv solution (4 mg/ml). This mixture was incubated in a water bath at 37° C. for one hour followed by centrifugation at 2000 g and used as inoculum for ducklings (50 μl/bird). Two groups of ducklings were used. Group A animals were inoculated with picroliv treated DHBV positive serum sample Group B ducklings (controls) were inoculated with DHBV positive serum sample. The animals were followed for a period of 4 weeks and at the end of the experiment they were sacrificed and the blood was collected for virological studies.

In the ducklings inoculated with the picroliv treated DHBV positive serum samples, 80% did not develop viremia at the end of 4 weeks whereas all the animals inoculated with only DHBV positive serum sample became viremic by this time.

The above findings suggested that in the picroliv treated serum samples binding occurred with the virus thereby making it noninfectious. To evaluate the duration of effect of picroliv after in vitro treatment with DHBV positive serum sample and the DHBV positive serum samples were treated with picroliv for 1, 3 and 6 hours at 37° C. in a water bath and subsequently inoculated to the ducklings which were sacrificed after 4 weeks. It was observed that the duration of picroliv treatment with DHBV did not modify its effects on DHBV infection.

Picroliv possessed marked immunostimulant activity in doses of 5 and 10 mg/kg×7 days as evidenced by PFC assay, HA titre, macrophage migration index, DTM response, macrophage activation and mitogenic response of lymphocytes. A nonspecific immunostimulatory response was also observed against *Leishmania donovani* infection in mastomys at the dose of 10 mg/kg×7 days of picroliv.

Picroliv was free from any significant CNS, CVS, autonomic and other systemic effects. It produced 42% reduction of paw oedema of rats induced by carrageenin at a dose of 165 mg/kg p.o.

The $LD_{50}$ of picroliv by i.p. route in mice was found to be 2026.9 mg/kg. By oral route it was 2500 mg/kg in mice and rats. In subacute toxicity study in a 90 day schedule picroliv was found to be safe in rat and monkey.

Although cucurbitacin glucoside (III) was a known compound, its biological activity is reported here for the first time. At a dose of 0.48 mg/kg, it provided significant protection against thioacetamide induced decrease in levels of DNA (94%), RNA (95%) and glycogen (60%) in liver in rat. At higher dose (1 mg/kg) also, it reversed the decrease in levels of DNA (56%), RNA (100%) and glycogen (36%). In addition, toxicant-induced increase in activity of acid ribonuclease and decrease in activity of succinate dehydrogenase were also reversed significantly by the higher dose of cucurbitacin glucoside.

At a higher dose (1 mg/kg) cucurbitacin glucoside showed more marked activity. The activities of γ-glutamyl transpeptidase and cytochrome $P_{450}$ were significantly restored. The levels of DNA, RNA and glycogen also showed significant reversal. The serum levels of GOT and GPT were restored almost completely towards normal after administration of cucurbitacin.

Cucurbitacin glucoside and fraction, F006, also afforded significant protection against the activities of 5'-nucleotidase (46-56%), acid ribonuclease (48-96%), glucose-6-phosphatase (46-61%) and levels of DNA (55-78%), protein (96-100%) and phospholipids. The decreased level of RNA was completely reversed by F006. The increased level of total lipids showed significant recovery (44-55%) after administration of cucurbitacin glucoside and F006. A significant lowering in the levels of GOT and GPT in serum was observed only with F006, but levels of bilirubin and protein in serum recovered with both the agents.

Cucurbitacin glucoside and fraction F006, at a dose of 1 mg/kg po×15 days, provided marked protection against hepatic damage caused by *Plasmodium berghei* infection in mastomys as manifested by the reversal of biochemical parameters in both serum as well as liver.

The effect of cucurbitacin glucoside and F006 was also studied on paracetamol-toxicated isolated rat hepatocytes (ex vivo). At the doses of 0.5 and 1 mg/kg po×7. Cucurbitacin glucoside provided 97.4 and 100% protection respectively by Trypan blue exclusion test. The rates of oxygen consumption at these doses were 100%. Fraction F006 also showed significant reversal of the reduced viability of the cells due to paracetamol at the doses of 0.5 mg/kg and 1 mg/kg viz. 89 and 97.2% (Trypan blue exclusion test) and 97.6 and 100% (oxygen uptake test).

Cucurbitacin glucoside and fraction F006 also showed significant choleretic as well as anticholestatic effects. Thus at the doses of 0.5 and 1 mg/kg the increase in the volume of bile was 38 and 90% respectively. Significant increase in bile salt as well as bile acids was also noticed at the above two doses viz. bile salts (40 and 100%) cholic acid (38.5 and 100% ) and deoxychloric acid (47.6 and 100%). With F006 marked increase of 28 and 30% bile flow was noticed at 0.5 and 1 mg/kg doses. Moderate to significant rise in the bile salts (30 and 87.5%), cholic acid (27 and 100%) and deoxycholic acid (22 and 65%) was also found at the above two doses.

The dose of 0.5 and 1 mg/kg po×7 cucurbitacin glucoside completely reversed the paracetamol induced decrease in bile flow, bile salts and bile acids. Fraction F006 afforded complete reversal in all the three parameters (bile flow, bile salts and bile acids) with the doses of 0.5 and 1 mg/kg against paracetamol induced cholestasis.

According to the present invention this is a process for the preparation of a fraction mainly containing (a) 1a,1b,2,5a,6,6a-hexahydro-6-hydroxy 1a (hydroxy methyl)-oxireno[4,5]cyclopenta (1,2-c) pyran-2yl-6-(3-phenyl-2-propanoate), [1a S-(1aα-1bβ,2β(E),5aβ,6β,6aα]-β-D-glycopyranoside (Picroside I), (b) 1a,1b,2,5a,6,6a-hexahydro-6-hydroxy-1a [(4-hydroxy-3-methoxy benzoyl)oxy]methyl]oxireno[4,5]-cyclopenta (1,2-c) pyran-2-yl-β-D-glucopyranoside (kutkoside) and (c) other unidentified substances, the amount of (a) and (b) ranging from 50–70%, the ratio of (a) and (b) being 1:1.5 to 1:2 by weight, the amount of (c) being 30–50%, that comprises.

(i) Extracting the root and/or rhizome powder of the plant *P. kurrooa* with a polar solvent and partitioning with a mixture of polar solvent and water to form a solvent and an aqueous layer.

(ii) Treating the aqueous layer again with polar solvent or a mixture of polar solvents to form an aqueous layer and a solvent layer.

(iii) Washing the solvent layer with water.

(iv) Treating the washed layer with decolourizing agent such as charcoal.

(v) Evaporating the bleached product to dryness.

(vi) Macerating the dried product with nonpolar solvent for removing less polar impurities.

The extraction of the root and/or rhizome of *P. kurrooa* may be carried out in any polar organic solvent such as aliphatic alcohol of 1 to 3 carbon atoms, Alcohol is preferred as maximum extraction is achieved in this case. Ethyl acetate is preferred in the step (ii) as it is cheap, non-toxic and non-hazardous and can also be easily recovered and reused. In step (iii) the preferred solvent may be ethanol, methanol, propanol-1, propanol-2, dioxan and the like. The maceration step can be preformed by treating with chloroform or any other non-polar solvent such as benzene, toluene and the like. Coloured impurities in the fraction can be minimised by stirring the solution obtained in step (iv) with active charcoal or with silica gel by just mixing the drug with it in the ratio of 1:2 and then eluting with polar solvent mixture.

The treatment with charcoal is more economical than the treatment with silica gel because of relatively higher cost of silica gel and adsorption of the fraction in silica gel would lead to lower recovery which may be a disadvantage.

We have found that it is also possible to extract the root and/or rhizome of the plant *Picrorhiza kurrooa* with alcohol and treat the extract with silica gel to form a free flowing solid when the extractive is adsorbed by the silica gel from which the fraction stated above is extracted by treatment with polar solvent. Since the process requires large volumne of polar solvent and costly silica gel it may not be commercially viable.

The process for the preparation of the fraction named by us as picroliv from the alcoholic extract of *P. kurrooa* having heptatoprotective immunostimulant and virus neutralizing activities is illustrated by the following examples.

EXAMPLE 1

(i) Ethanolic extractive (10 g) is dissolved in water (60 ml), (ii) aqueous solution is extracted with ethyl acetate (6×10 ml) and the ethylacetate layer is discarded, (iii) the aqueous solution from the previous step is now extracted with ethyl acetate containing 10% ethanol (6×40 ml) and the aqueous layer is washed with water (15 ml) and the aqueous layer is discarded, (v) the ethyl acetate-ethanol layer from the previous step is treated with charcoal (50 mg) and filtered, (vi) the filtrate is evaporated to dryness, (vii) the residue from step (vi) is macerated with chloroform (30 ml) and the solvent is decanted to give a chloroform insoluble product (2.1 g) with a 57% picroside I+kutkoside content.

EXAMPLE 2

(i) Ethanolic extractive (10 g) is dissolved in water (50 ml), (ii) aqueous solution is extracted with ethyl acetate (6×10 ml) and the ethyl acetate layer is discarded, (iii) the aqueous solution from step (ii) is now extracted with ethyl acetate containing 15% methanol (6×40 ml) and the aqueous layer is discarded, (iv) the ethyl acetate-ethanol layer is washed with water (3×10 ml) and the aqueous layer is discarded, (v) the ethyl acetate-ethanol layer from the previous step is evaporated to dryness, (vi) the residue from step (v) is macerated with chloroform (30 ml) and the solvent is decanted to give a chloroform insoluble product (2.5 g) with 56% picroside I+kutkoside content.

EXAMPLE 3

(i) Ethanolic extractive (10 g) is dissolved in a 50% aqueous methanol (15 ml), (ii) aqueous methanolic solution is extracted with chloroform (2×15 ml and 2×10 ml) and the chloroform layer is discarded, (iii) the aqueous methanolic solution from the previous step is extracted with ethyl acetate (2×25 ml and 2×15 ml), (iv) the aqueous methanolic layer from step (iii) is further diluted with 50% aqueous methanol (10 ml) and extracted with ethyl acetate (2×25 ml and 2×15 ml), (v) the ethyl acetate layer obtained in steps (iii) and (iv) are combined, treated with charcoal (1 g) and filtered, (vi) the filtrate is evaporated to dryness to give a residue (3.7 g) having picroside I and kutkoside content of 62%.

EXAMPLE 4

(I) Ethanolic extractive (50 g) is shaken with 10% aqueous acetone (350 ml), filtered and insoluble portion is discarded, (ii) aqueous acetone solution from the previous step is diluted with equal volume of acetone followed by addition of diethyl ether (100 ml) and the supernatant is separated from the percipitate by decantation, (iii) the percipitate is discarded and the supernatant is evaporated to dryness, (iv) residue obtained in the previous step is dissolved in acetone (120 ml) and a mixture of acetone+diethyl ether (1:1, 60 ml) is added, solution is decanted from the sticky precipitate and evaporated to dryness, (v) residue from the supernatant obtained in step (iv) is dissolved in acetone and diethyl ether is added, the supernatant is then decanted and evaporated to dryness, (vi) the process of partial precipitation is repeated six times, (vii) residue from the final diethyl ether acetone solution is macerated with chloroform and chloroform soluble portion is discarded. The chloroform insoluble portion (9 g) has picroside I+kutkoside content of 64%.

We claim:

1. A process for the preparation of a fraction of *Picrorhiza kurrooa* consisting essentially of (a) 1a,1b,2-,5a,6,6a-hexahydro-6hydroxy 1a (hydroxymethyl)-oxireno[4,5]cyclopenta (1,2-c) pyran-2-yl-6-(3-phenyl-2-propanoate),[1aS-(1aα-1bβ,2β(E),5aβ,6β,6,aα)]-β-D-glcopyranoside (Picroside I); (b) 1a,1b,2,5a,6,6a-hexahydro-6-hydroxy-1a [(4-hydroxy-3-methoxybenzoyl)oxy]oxy]methyl]oxireno[4,5]-cylopenta (1,2-c) pyran-2-yl-β-D-glucopyranoside (kutkoside) and (c) a fraction desiganated as F006 containing curcurbitacin glycosides, the total amount of (a) and (b) ranging from 50–70%, the ratio of (a) and (b) being 1:1.5 to 1:2 weight, the amount of (c) being 4–5% by weight said process comprising:

i) extracting the root and/or rhizome powder of the plant *P. kurrooa* with a polar solvent and partitioning with a mixture of polar solvent and water to form a solvent and an aqueous layer;

ii) treating the aqueous layer with the polar solvent or a mixture of polar solvents to form an aqueous layer and a solvent layer;

iii) washing the solvent layer with water; and iv) treating the washed layer with a decolorizing agent.

2. A process as claimed in claim 1 in which the polar solvent used is an alcohol of 1 to 3 carbon atoms.

3. A process as claimed in claim 1 wherein the extractive is dissolved in water.

4. A process as claimed in claim 1 wherein the aqueous solution is extracted with ethyl acetone.

5. A process as claimed in claim 1 wherein the ethyl acetate extracted aqueous solution from step (ii) is extracted with ethyl acetate containing a small amount of ethanol or methanol 6. A process as claimed in claim 5 in which the amount of ethanol or methanol used ranges from 10 to 15%.

7. A process as claimed in claim 1 wherein the extract is washed with water.

8. A process as claimed in claim 1 in which the decolourization is effected by treatment with characoal.

9. A process as claimed in claim 1 wherein decolourization is effected by treatment with silica gel in the ratio of 1:2 and eluting with a polar solvent or a mixture of polar solvents.

10. A process as claimed in claim 1 wherein the residue after drying is macerated with chloroform or any other nonpolar solvent.

* * * * *